United States Patent [19]
DeLaCroix et al.

[11] Patent Number: 5,206,177
[45] Date of Patent: Apr. 27, 1993

[54] APPARATUS FOR DETERMINING AN ANALYTE AND METHOD THEREFOR

[75] Inventors: Fern DeLaCroix; Johann Berger; Harvey Buck, all of Indianapolis, Indiana; Hans-Joachim Guder, Weilheim, Fed. Rep. of Germany

[73] Assignee: Boehringer Mannheim Corporation, Indianapolis, Ind.

[21] Appl. No.: 587,533

[22] Filed: Sep. 21, 1990

Related U.S. Application Data

[63] Continuation of Ser. No. 146,345, Jan. 21, 1988, abandoned.

[51] Int. Cl.$^5$ ........................................ G01N 33/533
[52] U.S. Cl. .................... 436/518; 435/7.1; 435/7.9; 435/7.92; 435/7.93; 435/7.94; 435/7.95; 435/962; 435/970; 435/973; 436/514; 436/530; 436/538; 436/541; 422/55; 422/56; 422/57; 422/58; 422/101
[58] Field of Search ............. 435/7.1, 7.9, 7.92–7.95, 435/962, 970, 973, 805; 436/514, 518, 530, 538, 541, 810; 422/55–58, 101

[56] References Cited

U.S. PATENT DOCUMENTS

| | | | |
|---|---|---|---|
| 4,042,335 | 8/1977 | Clement | 435/805 X |
| 4,094,647 | 6/1978 | Deutsch et al. | 436/810 |
| 4,144,306 | 3/1979 | Figueras | 422/56 |
| 4,166,093 | 8/1979 | Smith-Lewis et al. | 422/56 |
| 4,366,241 | 12/1982 | Tom et al. | 435/7 |
| 4,806,312 | 2/1989 | Greenquist | 422/56 |

FOREIGN PATENT DOCUMENTS 8702774 7/1987 World Int. Prop. O. ............. 435/7

Primary Examiner—Esther L. Kepplinger
Assistant Examiner—Carol A. Spiegel
Attorney, Agent, or Firm—Felfe & Lynch

[57] ABSTRACT

An apparatus for determining an analyte in a sample, as well as a method for carrying this out, are disclosed. The apparatus utilizes a first zone containing a labeled substance, and a second zone which permits separation of a mobile detectable moiety from unreacted reaction component. Detectable moiety is the product of reaction between reaction component and labeled substance.

45 Claims, 1 Drawing Sheet

APPARATUS FOR DETERMINING AN ANALYTE AND METHOD THEREFOR

This application is a continuation, of application Ser. No. 146,345, filed Jan. 21, 1988, now abandoned.

FIELD OF THE INVENTION

This invention relates to apparatus useful for determining one or more components in a sample, as well as methods for determining said components.

BACKGROUND

Chemical analysis of fluids, including body fluids such as blood, serum, urine, and so forth; water, fluid foodstuffs, etc., is often desirable and frequently necessary. Safety concerns, medical diagnosis, forensics, and other fields rely on determinations, either qualitative or quantitative, of components of fluids. These determinations, or assays, must be rapid and accurate.

A major field of clinical analysis is devoted to "dry chemistry" determinations of components in liquid samples. "Dry chemistry" refers to the apparatus used in the determinations, because the apparatus is dry to the touch. Generally, these apparatus take the form of monolayer and multilayer test strips and analytical test elements. These analytical devices have excellent storage and handling properties, and are convenient to use.

The determination of an analyte in a sample typically involves reacting the analyte with a binding partner which undergoes some type of change following reaction, leading to a detectable signal. While the change may be caused directly by the reaction with the analyte, frequently this is not the case, as the change usually results from some property produced by the interaction between analyte and reaction product which does not exist in unreacted components.

Several types of assay have been developed which utilize the above discussed principles. One important type is the immunoenzymometric assay. This test involves the binding of the analyte being tested with a reaction partner which carries a label. The binding partner is contained in a test strip or other apparatus in such a way that it is non-reactive unless and until its partner analyte contacts the test strip, in the form of a fluid sample. When this happens, the analyte and labeled binding partner bind to each other to form a complex, which must then be determined. This is accomplished by reacting the label carried by the binding partner with another substance so as to form a detectable signal. When the label is an enzyme, as it frequently is, the substance used is a substrate for the enzyme which, upon reaction with the enzyme, either forms a visible color or changes color. Measuring the change or amount of color gives a measure of complex, and hence of analyte.

A problem with this system, is that one must, have sufficient labeled binding partner to bind essentially all of analyte in the sample. The amount of analyte, however, is not known. This thus makes it necessary to provide excess amounts of labeled binding partner. Some of this will not react with analyte, but as it carries the label, it nonetheless forms a detectable signal. Thus, unless one separates reacted label carrier from the unreacted portion, no test result can be achieved.

Separation does, however, take place. An immunoenzymometric assay has an additional feature in that after the sample has contacted the labeled binding partner and some of the latter has been bound to form the complex, the mixture of complex and unreacted labeled binding partner is contacted to a sample of solid phase bound analyte or an analyte analogue which binds to uncomplexed labeled binding partner, and removes it from the solution mixture. One then has a clean division of labeled partner bound to analyte, and excess labeled binding partner bound to solid phase. Addition of substrate to either of these gives a color. If the amount of the labeled moiety with which one began is known, one measures the amount of signal either in the liquid phase, which gives a direct relationship to the amount of analyte, or in the solid phase, which provides an indirect relationship.

This type of assay involves two phases, and is thus called a heterogeneous assay. When performed using a test strip, one has the advantage of having labeled moiety, immobilized component, and reactive substance for the label all in one device. Fluid samples will diffuse through test strips, and thus the reactions will occur quickly and without the need for intervention by the investigator.

The immunoenzymometric assay is not the only type of assay used for these analytical systems. A competitive assay uses, rather than labeled binding partner, a sample of labeled analyte corresponding to the analyte being determined. The solid phase bound reactant, in these cases, is the binding partner for the analyte and labeled analyte. If any of the analyte is in the sample, competition for the binding sites ensues. One then measures the amount of label either in the solid phase or the liquid phase in the same manner described for immunoenzymometric assays, to determine the analyte.

Yet another system, which bears some relationship to the competitive assay, is the displacement assay. In this system, labeled analyte is already bound to a solid phase. When the sample contacts the test strip containing the bound labeled analyte, some of the label will be displaced by the binding between sample analyte and solid phase bound binding partner, and again, measurement in one of the phases is carried out.

Still another system which may be mentioned is a sandwich assay. Sandwich assays encompass a broad range of types of assays. For the invention described herein, however, a sandwich assay refers to formation of a complex between the analyte An being determined, a labeled, epitopically active fragment Fab* of a monoclonal antibody, and a nonlabeled whole monoclonal antibody mAb. The sandwich which forms when analyte contacts a test strip containing diffusible mAb and Fab* is mAb-An-Fab*. This sandwich contacts a solid phase containing another antibody, which binds to mAb, but not to Fab*. The result of this is to separate complex from uncomplexed Fab*, so as to permit determination in the same manner discussed supra for other systems. The prior art, which is discussed infra gives many examples of different forms of these systems.

PRIOR ART

The following discussion presents a review of all of the art found which relates in any way to the invention disclosed herein.

Baier, et al., U.S. Pat. No. 4,670,383 teaches an immunoenzymometric assay system. The assay involves adding a first antibody (or fragment) which carries a label to a sample, and then addition of solid phase bound antigen to pick up excess labeled antibody. This first solid phase is removed. The liquid phase containing labeled antibody-antigent complex is left, and to this is added a second antibody which binds either the first antibody, or to the antibody-antigen complex. It is this second step which allows for measurement of the amount of antigen in the sample.

Deutsch, et al., U.S. Pat. No. 4,477,576 also involves a system similar to the Baier system. The patent discloses a method whereby labeled antibody is added to an antigen containing sample. Following this the sample is combined with solid phase bound antigen. Some labeled antibody binds in solution, and some to solid phase antigen. The solid is then removed, and is immersed in a solution containing enzyme substrate. This results in a product which can be measured, and hence the amount of antigen may be determined.

No means are taught whereby the "mobile detectable moiety" (i.e., the unbound Ab*-Ag complex) is separated from solution. In fact, the solution complex never touches the substrate.

Berke, et al., U.S. Pat. No. 4,459,358 teaches an assay where a sample being analyzed contacts a carrier containing a binding partner which, if it does not complex, diffuses out of position. It is not solid phase bound, and is not immobilized. This diffusable binding partner moves to a second zone, where it is picked up by an immobilized species which prevents "backwash". This patent lacks any teaching or suggestion of an immobilized reaction partner in the first zone. Nothing is taught as to how one could measure an enzyme labeled, diffused antigen or antibody.

Liotta, U.S. Pat. No. 4,446,232 teaches a device which can be used in competitive displacement or immunoenzymometric assays. In the first part (or zone) of the device, one has immobilized antigens, and labeled antibodies. When a sample containing antigen is added to the device the antigen in the sample competes with the immobilized antigen for labeled antibody. Those labeled antibodies which do not bind to the solid phase bound antigen diffuse into a second zone, where a means is present to form a detectable signal with the labeled antibodies.

Deutsch, et al., U.S. Pat. Nos. 4,361,537 and 4,235,601 are related as continuation and parent. They concern a test strip ('537), and the method of using it. ('601). Only the test strip itself is considered here.

Various embodiments of test strips are disclosed, including one where a solid phase bound binding partner is used. When an immobilized form is used, however, no provision is made for measuring anything in this system but the immobilized form of labeled moiety. This is also the case in the disclosed "rate of flow" type of system, where an immobilized form is not used. These systems rely on the difference in diffusion rate between complexes and uncomplexed moieties. Only complexed material is measured.

The '537 patent is directed to products. Deutsch, et al. rely on differential rate of diffusion between complex and uncomplexed materials. Column 16, lines 7-13 of Deutsch, et al. (either one) show this in particular. Deutsch, et al., require a retarding element (which can be the test paper itself), which slows capillary transport of a "moving element". The "moving element" is one of either the reaction product (i.e., the complex), or the first reagent (i.e., the label). "Slowing" of one to separate two implies that both are moving. In other terms, Deutsch, etal. lacks a solid phase bound partner which removed substances from solution phase.

Mochida, et al., U.S. Pat. No. 4,200,436 describes an assay using a Fab or Fab' fragment which carries a label and then binds to an analyte in a sample. The complexes are separated from uncomplexed Fab, e.g., using a solid phase. Mochida, et al. does disclose the possibility of measuring non-solid phase bound material. This is done by adding a substrate which reacts with the label. There is no teaching or suggestion of a separation means or of a flow regulator.

Figueras, U.S. Pat. No. 4,144,306 teaches an analytical device which contains a "reagent layer" containing a "non-diffusable material" which is a "detectable moiety" and which reacts with an analyte. This can be, e.g., a labeled antibody. When the non-diffusable material reacts with the sample, it becomes diffusible and moves to a second layer where it can be detected (the "registration layer"). Measurement can be made of material in either layer.

Behringwerke European Patent Application 186 799 teaches various test strips which can be used in different types of assays, including IEMAs, competitive, and sandwich assays. Its broadest claim sets forth an apparatus which contains a "mobile phase application zone" ("MPAZ") an "adsorptive zone" ("AZ") a "labeled reactant zone" ("RZ"), and a "solid phase zone" ("SPZ"). The claims require a specific physical relationship among these four zones.

It is noted that pages 6 and 7 of the Behringwerke disclosure require that the reagent required for detection (i.e., the enzyme substrate), be added "after the separation stage" and "after the solid phase has been adequately washed". All of the discussion at pages 6-7 require a washing step, most certainly to remove uncomplexed label from the system. As the device is characterized by fluid contact between the various zones, washing the solid phase will result in the washing liquid removing everything uncomplexed. There is no possibility of ion exchange, e.g., in the Behringwerke disclosure.

Liberti: PCT Application PCT/US86/00668.

This patent deals with a "semi-quantitative" assay for determining whether an analyte is present in a sample over a baseline amount. This is performed by providing a test strip which contains a known amount of fixed binding complement which react with, and immobilize the analyte being determined. Also added to the solid phase are labeled analytes which will also react with the binding complement. This is used in a known amount as well. Because both react with the solid phase, one can determine how much label binds when a given amount of analyte is present in the sample. If "X" is the amount of solid phase, and "Y" is the baseline amount of analyte, then X—Y=Z, and Z is he amount of label which should bind. If the actual value obtained is less than "Z", then the analyte is present in an amount over the baseline figure. "Spillover" of labeled material can be measured. Liberti needs a device where the solid phase is present in excess as compared to the expected amount of analyte or labeled analyte. Further, Liberti clearly states that the invention is directed to a homogeneous assay, i.e.:

"The array (sic) of the present invention is described as a homogeneous array, in that no separation of bound and free specific binding pair substance is required." (page 9, lines 6-9).

Krauth, European Patent Application 122 695 (now U.S. Pat. No. 4,666,866) teaches an assay which depends on the use of whole antibodies, which have two binding sites for antigens. A solid phase is used which binds only to antibodies which are not completely saturated with antigen. In other words, the solid phase will bind unbound regions of antibodies.

Greenquist, European Patent Application 212 599 (Miles)

This application, to which U.S. Pat. No. 4,806,312 corresponds, '599 teaches separating labeled, unreacted reagent which passes into the second zone of a test strip. The label, however, forms a detectable composition when immobilized and not before. the Greenquist application.

Greenquist, European Patent No, 212 603 (Miles)

This patent application is also directed to immobilizing non-reacted labeled material. The '603 application, however, immobilizes the material before a detectable complex forms, after which a substrate is added.

The existence of so much patent literature indicates that heterogeneous assay test strips did not solve every problem, and actually new ones were created, in many respects.

One problem which occurs in heterogeneous assay test devices of the type discussed supra is the difficulty of reading the test strip following the assay. Many of the substrates used in enzyme label systems are themselves colored. Cleavage of the substrate by the enzyme frequently causes a change amounting only to sharing of one electron over the whole substrate molecule, and results in a color shift. This can be a very small shift, i.e., from 0-150 nm in wavelength, with an "observable" difference of, e.g., yellow to dark yellow. The change is so small that, taken with the presence of interference from the background of unreacted substrate, the difficulty in reading the change is increased. Another problem arises when the color of the reaction product being determined is a light one. Test strips are frequently, if not always, comprised almost entirely of white paper. Light colors are lost against the white background, particularly when the amount of reacted substrate is small.

These problems have now been addressed by the invention described herein. The invention provides an apparatus which can be used in a heterogeneous assay.

SUMMARY OF THE INVENTION

Hence it is an object of the invention to provide an apparatus for determining one or more analytes in a fluid sample, which also allows for separation of one of a product of a label and its reaction component and unreacted reaction component to provide for improved analyte analyses.

It is a further object of the invention to provide an apparatus for determining one or more analytes in a fluid sample, which includes a flow regulating means for regulation of the passage of the sample through the apparatus.

It is yet a further object of the invention to provide an apparatus for determining one or more analytes in a fluid sample which provides for both separation and flow regulation.

Still another object of the invention is to provide various methods for determining one or more analytes in solution, using the apparatus described herein.

DETAILED DESCRIPTION OF PREFERRED EMBODIMENTS

Figure 1:
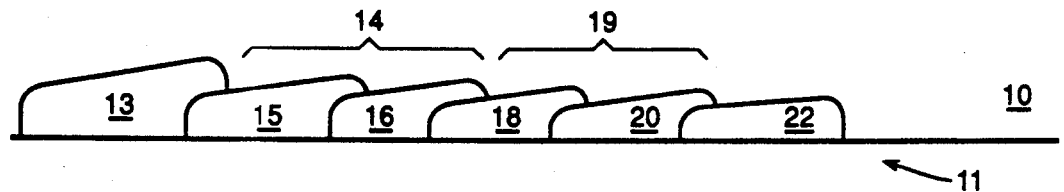
FIG. 1 shows an embodiment of the invention using a separating means in the second zone.

FIG. 1 shows means for separating mobile detectable moiety from unreacted reaction component. Specifically, with reference to the figure the apparatus 10 includes a carrier foil 11, which is a backing for the additional components. This is generally, although not necessarily, made of plastic. Other than providing physical support to the strip, it has no other function.

An optional sponge 13 is provided. This feature of the device can be impregnated, with a buffer, and may receive the sample being analyzed. It will be understood, however, that the sample may be introduced at other positions in the device.

The first zone 14 is positioned so that it receives sample which diffuses from sponge 13 when the sponge is used. If it is not, sample may be added directly to the first zone. This zone 14 contains a conjugate pad 15, and a matrix 16. While this figure shows these as separate parts of the first zone, it will be understood by the skilled artisan that they may be of one piece, especially when a displacement assay is being run.

Referring to FIG. 1, however, conjugate pad 15 contains the removable labeled analyte, labeled analyte analogue, or labeled binding partner. When the sample contacts this region, either by direct contact or by diffusion, the conjugate and the sample mix, and any reactions between analyte and binding partner take place. The mixture passes to matrix 16, which contains an immobilized form of a reagent. Generally the immobilized reagent is identical, or epitopically equivalent to the analyte being determined. When this is the case, the immobilized reagent must be present in an amount sufficient to bind essentially all of the labeled conjugate present in conjugate pad 15. This is necessary to provide for the situation where the sample contains none of the analyte being determined. In the case of a competitive assay, the immobilized reagent binds to both analyte and labeled analyte. Again, there must be sufficient solid phase bound reagent such that if there is no analyte present, essentially all of the labeled analyte is reacted.

In a displacement assay, it will be understood that conjugate pad 15 and matrix 16 will, of necessity, be of one piece because the immobilized reagent will already have bound to it the labeled analyte or analyte analogue.

Second zone 19 contains two parts, but this is not necessarily so. Substrate pad 18 contains a substrate which reacts with the label on the labeled component to form a detectable signal. This may be, but need not be, an enzyme substrate. Trapper pad 20, which is key to the invention, is in fluid contact with the substrate pad 18, or, if 18 and 20 constitute one piece, this one piece second zone is in fluid contact with the first zone. The trapper pad 20 contains a means, such as ionic exchange paper, which traps either the reaction product of the label and substrate, or unreacted substrate.

Finally, in fluid contact with the second zone 19 is the waste pad 22, which is adapted for receiving excess fluid. Further, it absorbs any materials which may be removed when the test strip is washed. The waste pad 22 can, alternatively, be used as a measuring point. When separation of detectable moiety and unreacted reaction component takes place in the second zone 19, the element which is not trapped can be washed into the waste pad. This element, rather than the trapped element, can be measured as well as, or in preference to, the trapped element.

Figure 2:
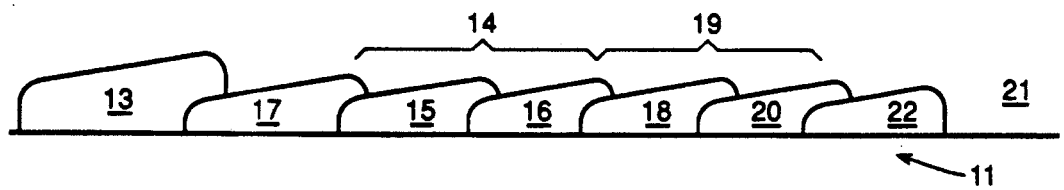
FIG. 2 shows an embodiment of the invention using both a separating means and a regulating means.

Another embodiment is shown in FIG. 2. This embodiment is identical to that shown in FIG. 1, except that it adds flow regulating means 17 to the device 21. The regulating means may contain substances, such as a buffer, which help to regulate flow of the analyte containing sample. Component 17 may be placed at various points in the apparatus. For example, it may be positioned in the first zone 14, such as between conjugate pad 15 and matrix 16 of FIG. 2; it may be between matrix 16 and substrate pad 18 in this figure, in the second zone, for , by being positioned between pads 18 and 20, or even at the end of the second zone and before the waste pad 22. The regulating means can be made of various substances, such as paper, which possess capillarity properties which differ from at least one of its neighbors.

Figure 3:
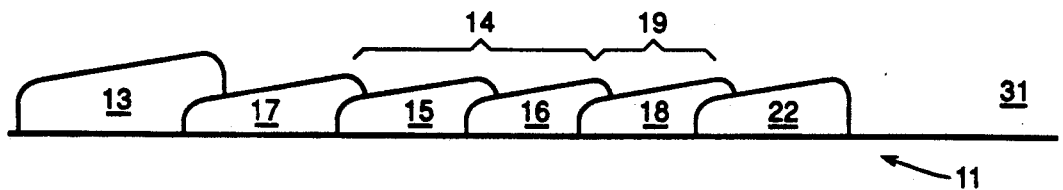
FIG. 3 depicts an embodiment of the invention using a regulating means, but no separating means.

FIG. 3 shows an embodiment identical to that of FIG. 2, but it lacks the trapper zone 20. The device depicted here has a component 17 which regulates flow of sample therethrough, with concentration of detectable moiety or unreacted reaction component.

The apparatus shown in FIGS. 1–3 are all usable for determining one or more analytes in any sample to be analyzed. For example, if the analysis being undertaken is to determine the presence of illicit drugs, a urine sample is taken from the subject and either sponge 13 is dipped therein, or a small dose of urine is added directly to the conjugate pad 15. When urine, e.g., is added directly to the first zone, 50 μl is sufficient. When the sponge is used, this generally holds about 1 ml.

Optionally additional material such as a "run buffer" or a washing solution may be used. In such cases, this material may be added at the same point as the sample or at some different point or points in the apparatus.

When sponge 13 is used, alone or with a buffer containing regulating means, the sample diffuses through 13 and 17, as provided in the device, until it reaches first zone component 15. Of course, if sample is added here directly, the diffusion through sponge 13 and 17 does not occur. In the first zone, the sample encounters enzyme labeled antibodies against the drug or drugs to be identified. If more than one drug is being assayed, each type of antibody may carry a different label but need not. Reactions occur between whatever drugs are present in the sample and the labeled antibodies. These complexes, plus any uncomplexed labeled antibody flows to that portion of the first zone 16 which contains immobilized reagents, in this case, immobilized drug or drugs which correspond to those being assayed. The immobilized drugs react with the uncomplexed antibodies, removing these from solution. The complex of drugs and labeled antibodies flow into the second zone 19, where substrate reacts with any label carried therein. If a trapper pad 20 is employed, as in FIGS. 1 and 2, this acts either to separate the reaction product of label and substrate from unreacted substrate, or unreacted substrate from the reaction product. When more than one drug is being tested, e.g., additional systems of substrate and enzyme are provided, each of which can be reacted and separated differentially. One then determines either reaction product or unreacted substrate in either the waste pad or the second zone. The determination step can be preceded by a washing step, if appropriate.

While the foregoing example was given for illicit drugs, different systems will be seen to be readily available to the skilled artisan. Among these substances which can be assayed include antibodies, antigens, and naturally occurring substances such as hormones, biological byproducts, and so forth. Viral infections, such as HIV, microbial or parasitic infections, such as Chlamydia, may be assayed as well. The test strips can be used to determine substances like glucose, various enzymes such as alpha amylase, and so forth.

Further particular embodiments will be seen from the following:

EXAMPLE 1

A test strip is prepared for analysis of thyroxin ($T_4$) in a fluid. The test strip is configured as is the device of FIG. 2. The first zone 14 contains antibodies to $T_4$ labeled with the enzyme beta-galactosidase (4U/ml), and $T_4$-succinimide ester which is immobilized onto CnBr activated paper (3512, Schleicher and Schuell). The regulating means 17 contains phosphate buffered saline (PBS) on Whatman 54 paper, and chlorophenol-red-beta-D-galactopyranoside (CPRG), a substrate for beta galactosidase, is impregnated into the second zone 19, together with an ion exchange trap (DE81, Whatman paper). CPRG, when unreacted, is yellow. Upon reaction with beta galactosidase, the reaction product is purple; however, when a separating means such as the ion exchange paper is not used, the resulting mixture of reaction product and unreacted CPRG is a muddy brown color. Neither the purple color indicative of the reaction nor the yellow color showing unreacted substrate is easily discernable. When the ion exchange paper is used, however, the purple color of the reaction product is concentrated and discernable from the yellow CPRG. If desired, unreacted yellow can be removed in a washing step.

EXAMPLE 2

Using the embodiment shown in FIG. 1, a test device is prepared to determine phenobarbital in a biological fluid.

Into the first zone 14 are incorporated antibodies to phenobarbital conjugated to horseradish peroxidase, and immobilized phenobarbital-succinimide ester, on CnBr activated paper as in Example 1. The second zone 19 contains the horseradish peroxidase substrate vanillin azine (0.5 mg/ml) which, in unreacted form, is yellow. The trap 20 is designed to pick up unreacted vanillin azine, but to pass the reaction product of horseradish peroxidase and vanillin azine, which is purple, into the waste zone 12.

EXAMPLE 3

This example uses the device shown in FIG. 3, and is designed for the determination of human chorionic gonadotropin (hCG), a pregnancy hormone. A conjugate of hCG specific antibody and beta galactosidase is incorporated into the first zone 14, together with hCG immobilized onto CnBr activated paper. The flow regulating means 17 contains PBS, and the second zone 14 contains resorufin-beta-D-galactopyranoside. Those complexes of hCG and conjugate which flow to the second zone react with the resorufin substrate forming an observable fuchsia color.

It will be understood by those skilled in the art that the particular materials used for the flow regulating means such as component 17 or the separating means such as trap 20, can and will vary. Different factors, such as the substrate used, the analyte being assayed, and the label determine what materials are used. Similarly, the substrate on pad 18 must be chosen so as to give some observable or detectable result when reacted with the label. Typically, the reaction is between an enzyme label and a substrate, but this is not the only possibility. For example, the label can be a fluorescent substance, and the reactive component a substance which caps or quenches the fluorescence. The label may itself be a cleavable substance and the the reactive component a substance which performs the cleavage, leading to color formation.

The apparatus has a plurality of zones, the first of which contains the reactive components for the analyte to be determined. Depending on the test system being used, some facets of the zone may vary. Typically, this zone will contain at least one immobilized reagent which binds to the analyte or analytes being determined. Typically, this immobilized reagent is a member of an antigen-antibody complex. This need not always be the case, however, as this immobilized reagent may be, e.g., protein A, a streptavidin-biotin complex, or any of the materials familiar to the skilled artisan. This zone also contains at least one of a labeled analyte, labeled analyte analogue, or labeled binding partner for the analyte being determined. The choice of what labeled moiety is used depends upon various parameters, such as reagent availability and cost. The label, typically, is an enzyme, but this is not essential. Systems are also envisioned where the label is, e.g., a fluorescent or radioactive substance, a portion of an enzyme which later binds to a complement to form a whole, operational enzyme, and other materials which will be recognized by the skilled artisan. When multiple analytes are being determined, of course, the different labeled analytes and so forth will differ. The label itself, however, can be the same or different for the plurality of labeled moieties. This is so because, even if the reaction between label and reactive component is the same with formation of the same detectable moiety, the difference in the analyte means that the different substances may separate differently. When a flow regulating means is incorporated, it may be any substance which has flow properties which differ from any part of the device. The flow regulating means may also have incorporated therein any of the various reagents described supra.

The second zone contains the reaction component which reacts with the label to form the detectable moiety. As was explained, this reaction component is typically an enzyme substrate, but it need not be drawn. In the case where multiple analytes are being determined, different reaction components may be used when the labels differ, but, as was pointed out, they do not need to be.

The separation means (trap 20) is preferably an ionic exchange means, such as ionic exchange paper, which has particular attraction for one of the detectable moiety or unreacted reaction component as compared to the other. Different types of separation means can be used as well, such as materials which, in connection with the detectable moiety and unreacted reaction component, have different degrees of hydrophobic interaction with the two. It is important to recognize that the interaction between separating means and the substance which separates out need not be a "chemical reaction" in the classic sense, i.e., that the separated substance undergoes chemical reaction which somehow alters the substance.

Various embodiments of the devices and methods described and claimed herein will of course be evident to the skilled artisan. The examples given herein are in no way to be construed as limitative of the broad disclosure.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. An apparatus for determining at least one analyte in a fluid sample, comprising:
   (a) a first porous zone comprising an immobilized, non diffusible reagent capable of specifically binding to at least one diffusible labeled reactant comprising a label conjugated to either said analyte, an analogue of said analyte or a specific binding partner for said analyte, and
   (b) a second porous zone comprising (i) a diffusible interactive reagent capable of reacting with the label portion of said diffusible labeled reactant to produce a diffusible detectable moiety and (ii) a means for separating said diffusible interactive reagent for said diffusible detectable moiety.

2. The apparatus of claim 1, wherein said first and second zones are in at least partial fluid contact with each other.

3. The apparatus of claim 1 wherein said first porous zone comprises two parts,
   (a') a first part comprising said at least one diffusible labeled reactant and
   (a") a second part comprising said immobilized, non-diffusible reagent which specifically binds to said at least one diffusible labeled reactant.

4. The apparatus of claim 1, wherein said second porous zone comprises two parts,
   (b') a first part comprising said reactive component and
   (b") a second part comprising said separating means.

5. The apparatus of claim 1, wherein said first and second porous zones each comprise two parts,
   (a') a first part of said first porous zone comprising a labeled, diffusible, specific binding partner for said analyte and
   (a") a second part of said first porous zone comprising said immobilized, non-diffusible reagent wherein said immobilized, non-diffusible reagent is capable of specifically binding to any labeled binding partner unbound to analyte,
   (b') a first part of said second porous zone comprising said diffusible interactive reagent capable of reacting with the label portion of said diffusible labeled reactant to produce a detectable moiety, and
   (b") a second part of said second porous zone comprising a means for separating said diffusible interactive reagent from said diffusible detectable moiety.

6. The apparatus of claim 3, wherein the first and second parts of said first porous zone are in at least partial fluid contact with each other.

7. The apparatus of claim 4, wherein the first and second parts of said second porous zone are in at least partial fluid contact with each other.

8. The apparatus of claim 5, wherein the second part of said first porous zone and the first part of said second porous zone are in at least partial fluid contact with each other.

9. The apparatus of claim 5, wherein the first part of said first porous zone is in at least partial fluid contact with the second part of said first porous zone, the second part of said first porous zone is in partial fluid contact with the first part of said second porous zone, and the second part of said second porous zone is in partial fluid contact with the first part of said second porous zone.

10. The apparatus of claim 1 wherein said separating means is an ion exchange paper capable of selectively retaining either said diffusible interactive reagent or said diffusible detectable moiety.

11. The apparatus of claim 1 wherein said first zone further comprises said at least one diffusible, labeled specific binding partner for said analyte.

12. The apparatus of claim 1 wherein said first zone further comprises either said at least one diffusible labeled analyte or said at least one diffusible labeled analogue of said analyte.

13. The apparatus of claim 1, wherein said first zone further comprises a plurality of different diffusible, labeled specific binding partners each type of which is capable of specifically binding to a separate analyte to be determined.

14. The apparatus of claim 1, wherein said first porous zone further comprises a plurality of one of (i) diffusible labeled analytes or (ii) diffusible labeled analyte analogues.

15. The apparatus of claim 11 wherein said at least one diffusible labeled specific binding partner for said analyte comprises an antibody or binding fragment thereof.

16. The apparatus of claim 13, wherein each of said diffusible, labeled specific binding partners comprises an antibody or binding fragment thereof.

17. The apparatus of claim 13, wherein said second porous zone further comprises a plurality of different diffusible interactive reagents, each type of which is capable of reacting with a specific diffusible, labeled binding partner to produce a specific diffusible, detectable moiety.

18. The apparatus of claim 14, wherein said second porous zone further comprises a plurality of diffusible, interactive reagents, each of which is capable of reacting with the label portion of a specific diffusible labelled analyte or a specific diffusible labeled analogue of said analyte.

19. An apparatus for determining at least one analyte in a fluid sample, comprising:
(a) a first zone comprising an immobilized, non-diffusible reagent capable of specifically binding to at least one diffusible reactant comprising analyte, labeled analyte, labeled analyte analogue or labeled analyte reaction partner,
(b) a second zone comprising (i) a diffusible interactive reagent capable of reacting with the label of said diffusible detectable moiety and (ii) a means for separating said diffusible interactive reagent from said diffusible detectable moiety, and
(c) at least one flow regulating means which regulates movement of a fluid sample introduced to said apparatus, wherein said flow regulating means has a flow rate different from the flow rate of at least a part of one of said first and second zones.

20. The apparatus of claim 19, wherein said first and second porous zones are in at least partial fluid contact with each other.

21. The apparatus of claim 19, wherein said first zone comprises two parts,
(a') a first part comprising said at least one diffusible labeled reactant, and
(a") a second part comprising said immobilized, non-diffusible reagent which specifically binds to said at least one diffusible labeled reactant.

22. The apparatus of claim 19, wherein said second porous zone comprises two parts,
(b') a first part which comprises said diffusible interactive reagent capable of reacting with the labeled portion of said diffusible labeled reactant, and
(b") a second part which comprises said flow regulating means.

23. The apparatus of claim 19, wherein each of said first and second porous zones comprises two parts, wherein said first zone comprises:
(a') a first part comprising said at least one diffusible labeled reactant, and
(a") a second part comprising said immobilized, non-diffusible reagent which specifically binds to said at least one diffusible labeled reactant, and said second zone comprises:
(b') a first part which comprises said diffusible interactive reagent capable of reacting with the labeled portion of said diffusible labeled reactant, and
(b") a second part which comprises said flow regulating means.

24. The apparatus of claim 19, wherein said flow regulating meas is incorporated in said first porous zone.

25. The apparatus of claim 19, wherein said flow regulating means is incorporated in said second porous zone.

26. The apparatus of claim 19, wherein said flow regulating means is positioned between said first and second porous zones.

27. The apparatus of claim 19, wherein said flow regulating means is positioned in said apparatus before said first porous zone and said second porous zone is positioned in said apparatus after said first zone.

28. The apparatus of claim 21, wherein the first and second parts of said first porous zone are in at least partial fluid contact with each other.

29. The apparatus of claim 22, wherein the first and second parts of said second porous zone are in at least partial fluid contact with each other.

30. The apparatus of claim 23, wherein the second part of said first porous zone and the first part of said second porous zone are in at least partial fluid contact with each other.

31. The apparatus of claim 23, wherein the first part of said first porous zone is in at least partial fluid contact with the second part of said first porous zone, said second part of said first porous zone is in partial fluid contact with the first part of said second porous zone, and said second part of said second porous zone is in partial fluid contact with the first part of said second porous zone.

32. The apparatus of claim 19, wherein said flow regulating means comprises filter paper.

33. The apparatus of claim 19, wherein said first zone further comprises at least one diffusible, labeled reactant comprising a label conjugated to a specific binding partner for said analyte.

34. The apparatus of claim 19, wherein said first zone further comprises at least one diffusible, labeled reactant comprising a label conjugated to either of said analyte or an analogue of said analyte.

35. The apparatus of claim 19, wherein said first zone comprises a plurality of diffusible labeled reactants, each type of which comprises a distinct label conjugated to a specific binding partner for a particular analyte.

36. The apparatus of claim 19, wherein said first zone further comprises a plurality of distinct types of diffusible labeled reactants, each type of which comprises a label conjugated to a different analyte or analyte analogue.

37. The apparatus of claim 33, wherein said at least one diffusible labeled specific binding partner for said analyte comprises an antibody or bindable fragment thereof.

38. The apparatus of claim 35, wherein said plurality of diffusible labeled specific binding partners for said analyte comprises antibodies or binding fragments thereof.

39. The apparatus of claim 35, wherein said second zone comprises a plurality of multiple, distinct diffusible interactive reagents, each of which is capable of reacting with a distinct label of said plurality of diffusible labeled reacts to produce a distinct diffusible detectable moiety.

40. The apparatus of claim 36, wherein said second zone comprises a plurality of multiple, distinct diffusible interactive reagents, each of which is capable of reacting with a distinct label of said plurality of labeled reactants.

41. The apparatus of claim 31, wherein said flow regulating means is positioned in said apparatus before said first process zone and said second porous zone is positioned after said first porous zone.

42. Method for determining at least one analyte in a fluid sample, comprising:
  (a) contacting said sample with a labeled binding partner which specifically binds to said analyte to form a mixture comprising (i) complexes of analyte and labeled binding partner and (ii) uncomplexed labeled binding partner,
  (b) contacting said mixture to an immobilized reagent which binds to uncomplexed labeled binding partner but not complexes of analyte and labeled binding partner, so as to remove uncomplexed labeled binding partner from said mixture,
  (c) contacting said mixture to an apparatus comprising a diffusible, interactive reagent capable of reacting with the label portion of said labeled binding partner to produce a detectable moiety in said mixture,
  (d) contacting said mixture with a means for separating detectable moiety from any unreacted diffusible interactive reagent, and
  (e) measuring one of unreacted diffusible interactive reagent, removed uncomplexed labeled binding partner or detectable moiety as a measure of analyte in said sample.

43. Method for determining at least one analyte in a fluid sample, comprising:
  (a) contacting said sample with a labeled reactant comprising a label conjugated to either said analyte or an analogue of said analyte, to form a mixture;
  (b) contacting said mixture with an immobilized binding partner capable of binding to said analyte and to said labeled reagent to form complexes of (i) immobilized binding partner and analyte, and of (ii) immobilized binding partner and labeled reagent,
  (c) contacting said complex containing mixture with an interactive reagent capable of reacting with the label portion of said labeled reactant to form a detectable moiety,
  (d) contacting said complex containing mixture with means for separating unreacted interactive reagent and detectable moiety from each other, and
  (e) measuring one of unreacted interactive reagent, immobilized labeled reagent or detectable moiety as a measure of analyte in said sample.

44. Method for determining at least one analyte in a fluid sample, comprising:
  (a) contacting said sample with a labeled reactant comprising a label conjugated to either said analyte or an analogue of said analyte, to form a mixture;
  (b) contacting said mixture with an immobilized binding partner capable of binding to said analyte and to said labeled reagent, to form complexes of immobilized binding partner and analyte, and of immobilized binding partner and labeled reagent;
  (c) separating said complexes from said mixture;
  (d) contacting complex free mixture with an interactive reagent capable of reacting with the label portion of said labeled reactant to produce a detectable moiety;
  (e) contacting said complex free mixture with a means for separating unreacted interactive reagent from said detectable moiety, and
  (f) measuring one of label in said separated complex detectable moiety or unreacted interactive reagent as a measure of analyte in said sample.

45. Method for determining at least one analyte in a fluid sample, comprising:
  (a) contacting said sample with a complex of labeled reactant capable of specifically binding to said analyte and an immobilized binding partner for said labeled reactant, so as to form a mixture of displaced labeled reactant complexed to said analyte and free labeled reactant;
  (b) contacting said mixture to an immobilized reagent capable of specifically binding to free labeled reactant but not to complexes of labeled reactant and analyte, so as to remove free labeled reactant therefrom;
  (c) contacting said mixture to an interactive reagent which reacts with the label of said labeled reactant to form a detectable moiety;
  (d) contacting said mixture with a separation means for separating interactive reagent from detectable moiety; and
  (e) measuring immobilized labeled reactant, unreacted interactive reagent or detectable moiety as a measure of analyte in said sample.

* * * * *